(12) United States Patent
Schiemann et al.

(10) Patent No.: US 8,524,732 B2
(45) Date of Patent: Sep. 3, 2013

(54) SUBSTITUTED TETRAHYDROQUINOLINES

(75) Inventors: Kai Schiemann, Seeheim-Jugenheim (DE); Dirk Finsinger, Darmstadt (DE); Christiane Amendt, Muehltal/Trautheim (DE); Frank Zenke, Darmstadt (DE)

(73) Assignee: MERCK PATENT GmbH, Darmstadt (DE)

( * ) Notice: Subject to any disclaimer, the term of this patent is extended or adjusted under 35 U.S.C. 154(b) by 769 days.

(21) Appl. No.: 12/532,002

(22) PCT Filed: Feb. 21, 2008

(86) PCT No.: PCT/EP2008/001353
§ 371 (c)(1),
(2), (4) Date: Sep. 18, 2009

(87) PCT Pub. No.: WO2008/113451
PCT Pub. Date: Sep. 25, 2008

(65) Prior Publication Data
US 2010/0022579 A1    Jan. 28, 2010

(30) Foreign Application Priority Data

Mar. 20, 2007  (DE) .......................... 10 2007 013 855

(51) Int. Cl.
*A61K 31/436* (2006.01)
*C07D 491/052* (2006.01)

(52) U.S. Cl.
USPC ............................................. 514/291; 546/89

(58) Field of Classification Search
USPC ........................................... 546/89; 514/291
See application file for complete search history.

(56) References Cited

U.S. PATENT DOCUMENTS 7,868,172 B2 * 1/2011 Schiemann et al. ............ 546/80
7,893,082 B2 * 2/2011 Schiemann et al. .......... 514/291

FOREIGN PATENT DOCUMENTS

| DE | 10 2005 027170 A1 | 12/2006 |
| WO | WO 2005/063735 A | 7/2005 |
| WO | 2007054138 | * 5/2007 |
| WO | WO 2007/054138 A | 5/2007 |

OTHER PUBLICATIONS

Terrago , 2008, Benzimidazolium Salts as Small, Nonpeptidic and BBBPermeable Human Prolyl Oligopeptidase Inhibitors.*
"International Search Report", International Application No. PCT/EP2008/001353, 3 pages, Publication Date Jun. 5, 2008, Date of Mailing Jun. 25, 2008.

* cited by examiner

*Primary Examiner* — Rita Desai
(74) *Attorney, Agent, or Firm* — Millen, White, Zelano & Branigan, P.C.

(57) ABSTRACT

Compounds of the formula (I), in which $R^1$, $R^2$, $R^3$, $R^4$, $R^5$, X, Y, W, $Q^1$, $Q^2$, Z, s and m have the meanings indicated in Claim 1, can be employed, inter alia, for the treatment of tumors.

16 Claims, No Drawings

SUBSTITUTED TETRAHYDROQUINOLINES

BACKGROUND OF THE INVENTION

The invention had the object of finding novel compounds having valuable properties, in particular those which can be used for the preparation of medicaments.

The present invention relates to compounds of the formula I and to the use thereof for the treatment and prophylaxis of diseases in which the inhibition, regulation and/or modulation of mitotic motor proteins, in particular the mitotic motor protein Eg5, plays a role, furthermore to pharmaceutical compositions which comprise these compounds.

In detail, the present invention relates to compounds of the formula I which which preferably inhibit, regulate and/or modulate one or more mitotic motor proteins, to compositions which comprise these compounds, and to methods for the use thereof for the treatment of diseases and complaints such as angiogenesis, cancer, tumour formation, growth and propagation, arteriosclerosis, ocular diseases, choroidal neovascularisation and diabetic retinopathy, inflammatory diseases, arthritis, neurodegeneration, restenosis, wound healing or transplant rejection. In particular, the compounds according to the invention are suitable for the therapy or prophylaxis of cancer diseases.

During mitosis, various kinesins regulate the formation and dynamics of the spindle apparatus, which is responsible for correct and coordinated alignment and separation of the chromosomes. It has been observed that specific inhibition of a mitotic motor protein—Eg5—results in collapse of the spindle fibres. The result of this is that the chromosomes can no longer be distributed correctly over the daughter cells. This results in mitotic arrest and can thus cause cell death. Upregulation of the motor protein Eg5 has been described, for example, in tissue from breast lung and colon tumours. Since Eg5 takes on a mitosis-specific function, it is principally rapidly dividing cells and not fully differentiated cells that are affected by Eg5 inhibition. In addition, Eg5 regulates exclusively the movement of mitotic microtubuli (spindle apparatus) and not that of the cytoskeleton. This is crucial for the side-effect profile of the compounds according to the invention since, for example, neuropathies, as observed in the case of Taxol, do not occur or only do so to a weakened extent. The inhibition of Eg5 by the compounds according to the invention is therefore a relevant therapy concept for the treatment of malignant tumours.

In general, all solid and non-solid tumours can be treated with the compounds of the formula I, such as, for example, monocytic leukaemia, brain, urogenital, lymphatic system, stomach, laryngeal and lung carcinoma, including lung adenocarcinoma and small-cell lung carcinoma. Further examples include prostate, pancreatic and breast carcinoma.

Surprisingly, it has been found that the compounds according to the invention effect specific inhibition of mitotic moter proteins, in particular Eg5. The compounds according to the invention preferably exhibit an advantageous biological activity which can easily be detected in the assays described herein, for example. In such assays, the compounds according to the invention preferably exhibit and cause an inhibiting effect, which is usually documented by $IC_{50}$ values in a suitable range, preferably in the micromolar range and more preferably in the nanomolar range.

As discussed herein, effects of the compound according to the invention are relevant to various diseases. Accordingly, the compounds according to the invention are useful in the prophylaxis and/or treatment of diseases which are influenced by inhibition of one or more mitotic motor proteins, in particular Eg5.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases, and also to a method for the treatment of the said diseases comprising the administration of one or more compounds according to the invention to a patient in need of such an administration.

It can be shown that the compounds according to the invention have an advantageous effect in a xenotransplant tumour model.

The host or patient can belong to any mammal species, for example a primate species, particularly humans; rodents, including mice, rats and hamsters; rabbits; horses, cattle, dogs, cats, etc. Animal models are of interest for experimental investigations, providing a model for the treatment of a human disease.

The susceptibility of a certain cell to treatment with the compounds according to the invention can be determined by testing in vitro. Typically, a culture of the cell is combined with a compound according to the invention at various concentrations for a period which is sufficient to enable the active ingredients to induce cell death or inhibit migration, usually between approximately one hour and one week. For testing in vitro, cultivated cells from a biopsy sample can be used. The viable cells remaining after the treatment are then counted. The dose varies depending on the specific compound used, the specific disease, the patient status, etc. Typically, a therapeutic dose is sufficient considerably to reduce the undesired cell population in the target tissue, while the viability of the patient is maintained. The treatment is generally continued until a considerable reduction has occurred, for example at least about a 50% reduction in the cell burden, and can be continued until essentially no undesired cells are detected in the body.

SUMMARY OF THE INVENTION

Compounds of the formula I

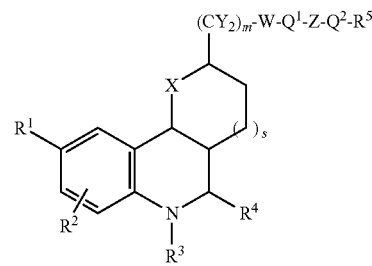

in which
$R^1$ denotes H, A, Hal, SA, $(CH_2)_pCN$, SCN, $(CF_2)_pCF_3$, $SF_5$, OA, $O(CF_2)_pCF_3$, $S(CF_2)_pCF_3$, $NR_2$, NRCOR, $NRSO_2R$, $NR(CH_2)_pNR_2$, $CONR(CH_2)_pNR_2$, $SO_2NR(CH_2)_pNR_2$, $CONR_2$, $SO_2NR_2$, COOR,
$R^2$ denotes H, Hal,
$R^3$ denotes H, A
A denotes linear or branched alkyl having 1 to 10 C atoms or cycloalkyl having 3 to 7 C atoms,
$R^4$ denotes aryl or heteroaryl, each of which is unsubstituted or mono- or polysubstituted by aryl or heteroaryl, each of which may be substituted by Hal, $NO_2$, CN, A, OR, OCOR, $NR_2$, $CF_3$, $OCF_3$, $OCH(CF_3)_2$, or by Hal, $NO_2$, CN, OR, A, $-(CY_2)_n-OR$, $-OCOR$, $-(CY_2)_n-CO_2R$, $-(CY_2)_n-CN$ or $-(CY_2)_n-NR_2$, Y denotes H, A, Hal, OR, R denotes H, A, $(CH_2)_pO(CH_2)_pR^3$, $(CH_2)_pNA(CH_2)_pR^3$, W denotes $CH_2$, C=O, C=S $Q^1$ denotes NR, O, S Z denotes $-SO_2-$, $-SO-$,

[chemical structures]

$Q^2$ denotes NR, S, O or a single bond, $R^5$ denotes H, $(CY_2)_pNR_2$, $(CY_2)_pOR$, $(CY_2)_pSR$,

[chemical structure]

$(CY_2)_pQ^1COQ^1R$, $(CY_2)_pCOOR$ and, if $Q^2$ denotes a single bond, also Hal, Hal denotes F, Br or Cl n denotes 1, 2, 3 or 4, m denotes 0, 1 or 2, p denotes 0, 1, 2, 3, 4, 5, 6, 7 or 8 and s denotes 0, 1 or 2, and pharmaceutically usable derivatives, solvates, tautomers, salts and stereoisomers thereof, including mixtures thereof in all ratios.

The invention also relates to the optically active forms, the enantiomers, the racemates, the diastereomers and the hydrates and solvates of these compounds. The term solvates of the compounds is taken to mean adductions of inert solvent molecules onto the compounds of the formula I which form owing to their mutual attractive force. Solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

Similar compounds are described, for example, in Tetrahedron Lett. 1988, 29, 5855-5858, Tetrahedron Lett. 2003, 44, 217-219, J. Org. Chem. 1997, 62, 4880-4882, J. Org. Chem. 1999, 64, 6462-6467, Chem. Lett. 1995, 423-424, J. Org. Chem. 2000, 65, 5009-5013, Chem. Lett. 2003, 32, 222-223, US2003149069A1, but are not mentioned in connection with cancer treatments and/or do not contain the features essential to the invention.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which causes at least one of the following effects in a human or another mammal (compared with a subject who has not received this amount):

improvement in the healing treatment, healing, prevention or elimination of a disease, syndrome, condition, complaint, disorder or side-effects or also the reduction in the progress of a disease, complaint or disorder.

The term "therapeutically effective amount" also encompasses the amounts which are effective for increasing or enhancing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to the patent claims and pharmaceutically usable derivatives, salts, solvates and stereoisomers thereof, characterised in that For the preparation of compound of the formula I in which W denotes $CH_2$, compounds of the formula II

[chemical structure] II in which $R^1$, $R^2$, $R^3$, $R^4$, X, Y, $Q^1$, s and m have the meanings indicated above, are reacted with compound of the formula III $L-Z-Q^2-R^5$ III in which Z, Q², R⁵ have the meanings indicated above

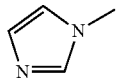

and L denotes a leaving group, preferably Br, Cl, OA, or OCOA, and the resultant compounds of the formula I in which W denotes CH₂ are converted into the further compounds of the formula I by generally known process steps.

Any mixtures of diastereomers and enantiomers of the compounds of the formula I obtained by the process described above are preferably resolved by chromatography or crystallisation.

If desired, the bases and acids of the formula I obtained by the process described above are converted into their salts.

Above and below, the radicals Hal, R, R¹, R², R³, R⁴, R⁵, W, Q¹, Q², Z, m, n, s and p have the meanings indicated for the formula I, unless expressly indicated otherwise. If individual radicals occur more than once within a compound, the radicals adopt the meanings indicated, independently of one another.

Alkyl is preferably unbranched (linear) or branched, and has 1, 2, 3, 4, 5, 6, 7, 8, 9 or 10 C atoms. Alkyl preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

Alkyl very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Alkyl also denotes cycloalkyl.

Cycloalkyl preferably denotes cyclopropyl, cyclobutyl, cylopentyl, cyclohexyl or cycloheptyl, but in particular cyclopentyl.

R¹, preferably denotes, alkyl, CF₃, OCF₃, SCN, CH₂CN, OH, S alkyl, O alkyl, Hal, SCF₃. In particular, R¹ denotes t-butyl, CF₃, Br, Cl, CF₃.

R² is preferably in position 8 on the tetrahydroclinoline skeleton and is preferably H or F, in particular H.

R³ is preferably H or methyl, ethyl, n-propyl or n-butyl, in particular H.

R⁴ is preferably aryl, which may be substituted by F, Cl, OR or aryl. In particular, R⁴ denotes phenyl, hydroxyphenyl or alkylphenyl.

R is preferably H, or A or (CH₂)ₚNA(CH₂)ₚ, R³

W is preferably CH₂ or C=O, in particular CH₂.

Q¹ is preferably NR or O, in particular NR. Q¹ very particularly preferably denotes NH.

Z preferably denotes

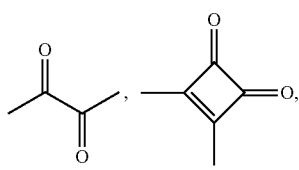

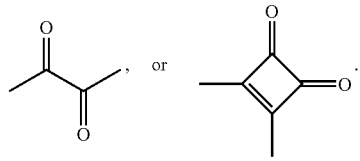

in particular

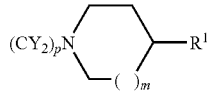

Q² is preferably NR, O or a single bond, in particular NH.
R⁵ is preferably H, (CY₂)ₚNR₂, (CY₂)ₚOR,

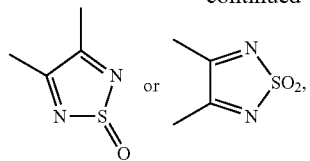

or (CY₂)ₚCOOR, in particular (CY₂)ₚNR.
Y preferably denotes H, A or F, in particular H.
n preferably denotes 0, 1, 2, or 3.
m preferably denotes 0 or 1, in particular 0.
p preferably denotes 0 or 2.
s preferably denotes 1.

Aryl preferably denotes phenyl, naphthyl or biphenyl, each of which is unsubstituted or mono-, di- or trisubstituted by Hal, A, OH, OA, NH₂, NO₂, CN, COOH, COOA, CONH₂, NHCOA, NHCONH₂, NHSO₂A, CHO, COA, SO₂NH₂, SO₂A, —CH₂—COOH or —OCH₂—COOH.

Aryl preferably denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4- methoxyphenyl, 3-amino-6-methylphenyl, 3-chloro-4-acetamidophenyl or 2,5-dimethyl-4-chlorophenyl.

Heteroaryl preferably denotes a mono- or bicyclic aromatic heterocycle having one or more N, O and/or S atoms which is unsubstituted or mono-, di- or trisubstituted by Hal, A, $NO_2$, $NHA$, $NA_2$, OA, COOA or CN.

Heteroaryl particularly preferably denotes a monocyclic saturated or aromatic heterocycle having one N, S or O atom, which may be unsubstituted or mono-, di- or trisubstituted by Hal, A, NHA, $NA_2$, $NO_2$, COOA or benzyl.

Irrespective of further substitutions, unsubstituted heteroaryl denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3, 4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

Hal preferably denotes F, Cl or Br, in particular F or Cl.

Throughout the invention, all radicals which occur more than once may be identical or different, i.e. are independent of one another.

The compounds of the formula I can have one or more chiral centres and therefore exist in various stereoisomeric forms. The formula I encompasses all these forms.

Particularly preferred compounds of the formula I are those of the subformulae IA to IC:

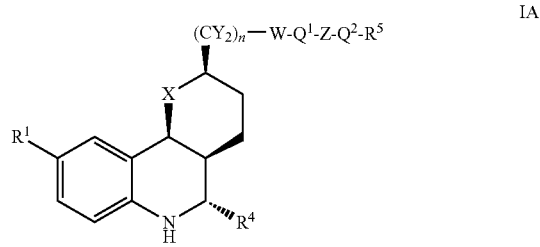

IA

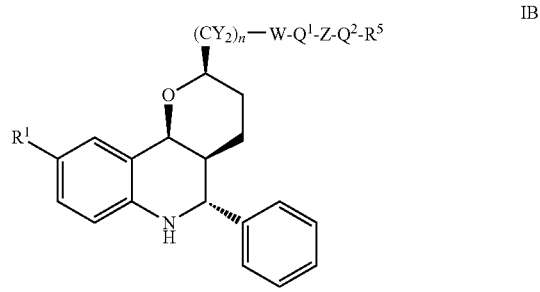

IB

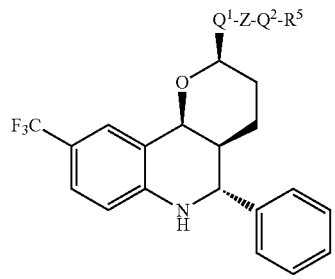

IC in which
Y, W, $Q^1$, $Q^2$, Z, $R^1$, $R^4$, $R^5$ and n have the meanings indicated above.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. The starting materials are preferably prepared in accordance with WO 2005/063735. Use can also be made here of variants known per se which are not mentioned here in greater detail.

If desired, the starting materials may also be formed in situ so that they are not isolated from the reaction mixture, but instead are immediately converted further into the compounds of the formula I.

The reactions of the compounds of the formula III with the compounds of the formula II are generally carried out in an inert solvent. Depending on the conditions used, the reaction time is between a few minutes and 14 days, the reaction temperature is between about 0° and 180°, normally between 0° and 100°, particularly preferably between 0° C. and 70° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane, or mixtures of the said solvents.

If desired, a functionally modified amino and/or hydroxyl group in a compound of the formula I can be liberated by solvolysis or hydrogenolysis by conventional methods. This can be carried out, for example, using NaOH or KOH in water, water/THF or water/dioxane at temperatures between 0 and 100°.

The reduction of an ester to the aldehyde or alcohol or the reduction of a nitrile to the aldehyde or amine is carried out by methods as are known to the person skilled in the art and are described in standard works of organic chemistry.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The medicaments from Table 1 are preferably, but not exclusively, combined with the compounds of the formula I. A combination of the formula I and medicaments from Table 1 can also be combined with compounds of the formula V.

TABLE 1

| Alkylating agents | Cyclophosphamide | Lomustine |
|---|---|---|
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | Chloroambucil | Temozolomide |
| | Dacarbazine | Semustine |
| | Carmustine | |

TABLE 1-continued

| | | |
|---|---|---|
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 (Hoffmann-La Roche) |
| | Ormiplatin | |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | |
| | Teniposide or mitoxantrone | Quinamed (ChemGenex) |
| | | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | | BNP-1350 (BioNumerik) |
| | Pixantrone (Novuspharma) | CKD-602 (Chong Kun Dang) |
| | Rebeccamycin analogue (Exelixis) | KW-2170 (Kyowa Hakko) |
| | BBR-3576 (Novuspharma) | |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazone | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantrone (Novantrone) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilone B (BMS) |
| | BMS 247550 (BMS) | BNP-7787 (BioNumerik) |
| | BMS 184476 (BMS) | CA-4 prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |

TABLE 1-continued

| Category | | |
|---|---|---|
| Thymidylate synthase inhibitors | Pemetrexed (Eli Lilly) ZD-9331 (BTG) | Nolatrexed (Eximias) CoFactor ™ (BioKeys) |
| DNA antagonists | Trabectedin (PharmaMar) Glufosfamide (Baxter International) Albumin + 32P (Isotope Solutions) Thymectacin (NewBiotics) Edotreotid (Novartis) | Mafosfamide (Baxter International) Apaziquone (Spectrum Pharmaceuticals) O6-Benzylguanine (Paligent) |
| Farnesyl transferase inhibitors | Arglabin (NuOncology Labs) Ionafarnib (Schering-Plough) BAY-43-9006 (Bayer) | Tipifarnib (Johnson & Johnson) Perillyl alcohol (DOR BioPharma) |
| Pump inhibitors | CBT-1 (CBA Pharma) Tariquidar (Xenova) MS-209 (Schering AG) | Zosuquidar trihydrochloride (Eli Lilly) Biricodar dicitrate (Vertex) |
| Histone acetyl transferase inhibitors | Tacedinaline (Pfizer) SAHA (Aton Pharma) MS-275 (Schering AG) | Pivaloyloxymethyl butyrate (Titan) Depsipeptide (Fujisawa) |
| Metalloproteinase inhibitors | Neovastat (Aeterna Laboratories) Marimastat (British Biotech) | CMT-3 (CollaGenex) BMS-275291 (Celltech) |
| Ribonucleoside reductase inhibitors | Gallium maltolate (Titan) Triapin (Vion) | Tezacitabine (Aventis) Didox (Molecules for Health) |
| TNF-alpha agonists/ antagonists | Virulizin (Lorus Therapeutics) CDC-394 (Celgene) | Revimid (Celgene) |
| Endothelin-A receptor antagonists | Atrasentan (Abbot) ZD-4054 (AstraZeneca) | YM-598 (Yamanouchi) |
| Retinoic acid receptor agonists | Fenretinide (Johnson & Johnson) LGD-1550 (Ligand) | Alitretinoin (Ligand) |
| Immuno-modulators | Interferon Oncophage (Antigenics) GMK (Progenics) Adenocarcinoma vaccine (Biomira) CTP-37 (AVI BioPharma) JRX-2 (Immuno-Rx) PEP-005 (Peplin Biotech) Synchrovax vaccines (CTL Immuno) Melanoma vaccine (CTL Immuno) p21-RAS vaccine (GemVax) | Dexosome therapy (Anosys) Pentrix (Australian Cancer Technology) JSF-154 (Tragen) Cancer vaccine (Intercell) Norelin (Biostar) BLP-25 (Biomira) MGV (Progenics) !3-Alethin (Dovetail) CLL-Thera (Vasogen) |
| Hormonal and antihormonal agents | Oestrogens Conjugated oestrogens Ethynyloestradiol Chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-Methoxyoestradiol (EntreMed) Arzoxifen (Eli Lilly) |
| Photodynamic agents | Talaporfin (Light Sciences) Theralux (Theratechnologies) Motexafin-Gadolinium (Pharmacyclics) | Pd bacteriopheophorbid (Yeda) Lutetium-Texaphyrin (Pharmacyclics) Hypericin |
| Tyrosine kinase inhibitors | Imatinib (Novartis) Leflunomide (Sugen/Pharmacia) ZDI839 (AstraZeneca) Erlotinib (Oncogene Science) Canertjnib (Pfizer) Squalamine (Genaera) SU5416 (Pharmacia) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) |

TABLE 1-continued

| | | |
|---|---|---|
| | SU6668 (Pharmacia) | MDX-H210 (Medarex) |
| | ZD4190 (AstraZeneca) | 2C4 (Genentech) |
| | ZD6474 (AstraZeneca) | MDX-447 (Medarex) |
| | Vatalanib (Novartis) | ABX-EGF (Abgenix) |
| | PKI166 (Novartis) | IMC-1C11 (ImClone) |
| | GW2016 (GlaxoSmithKline) | |
| | EKB-509 (Wyeth) | |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol ™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | Trans-retinoic acid (differentiator, NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimulant, GPC Biotech) | Urocidin (apoptosis promoter, Bioniche) |
| | CDA-II (apoptosis promoter, Everlife) | Ro-31-7453 (apoptosis promoter, La Roche) |
| | SDX-101 (apoptosis promoter, Salmedix) | Brostallicin (apoptosis promoter, Pharmacia) |
| | Ceflatonin (apoptosis promoter, ChemGenex) | |

The compounds of the formula I are preferably combined with known anti-cancer agents.

These known anti-cancer agents include the following: oestrogen receptor modulators, androgen receptor modulators, retinoid receptor modulators, cytotoxic agents, antiproliferative agents, prenyl-protein transferase inhibitors, HMG-COA reductase inhibitors, HIV protease inhibitors, reverse transcriptase inhibitors and other angiogenesis inhibitors. The present compounds are particularly suitable for administration at the same time as radiotherapy. The synergistic effects of inhibition of VEGF in combination with radiotherapy have been described by specialists (see WO 00/61186). "Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646. "Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)mu-[diamineplatinum(II)]bis-[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplastone, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797. Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4': b,7]indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]-glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino-[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-amino-pyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Particular preference is given to the use of the compound according to the invention for the treatment and prophylaxis of tumour diseases.

The tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention also encompasses a method for the treatment of a patient who has a neoplasm, such as a cancer, by administration of a) one or more of the compounds of the formula I:
b) and one or more of the compounds of the formula V or acid-addition salts thereof, in particular hydrochlorides:

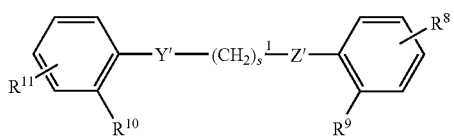

V

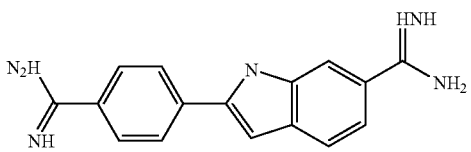

(G-3)

in which Y' and Z' each, independently of one another, denote O or N, $R^9$ and $R^{10}$ each, independently of one another, denote H, OH, halogen, OC1-10-alkyl, $OCF_3$, $NO_2$ or $NH_2$, s' denotes an integer between 2 and 6, each inclusive, and $R^8$ and $R^{11}$ are each, independently of one another, preferably in the meta- or para-position and are selected from the group:

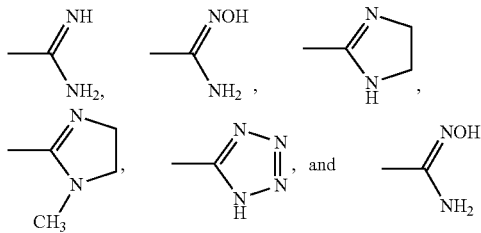

where the first and second compound are administered simultaneously or within 14 days of one another in amounts which are sufficient to inhibit the growth of the neoplasm.

The combination of the compounds of the formula I with the compounds of the formula V and other pentamedine analogues results in a synergistic action in the inhibition of neoplasias. Combinations comprising the compounds of the formula V are mentioned, for example, in WO 02058684.

The mechanism of action of pentamidine or derivatives thereof has currently not been clearly explained: pentamidine or derivatives thereof appears to have pleiotropic actions since it results in a decrease in DNA, RNA and protein synthesis. It was recently described that pentamidine is a capable inhibitor of PRL1, -2 and 3 phosphatases (Pathak et al., 2002) and tyrosine phosphatases, and overexpression thereof is accompanied by neoplastic malignant tumours in humans. On the other hand, it has been described that pentamidine is a medicament which binds to the DNA minor groove (Puckowska et al., 2004) and is able to exert its action via disturbance of gene expression and/or DNA synthesis.

Other suitable pentamidine analogues include stilbamidine (G-1) and hydroxystilbamidine (G-2) and indole analogues thereof (for example G-3):

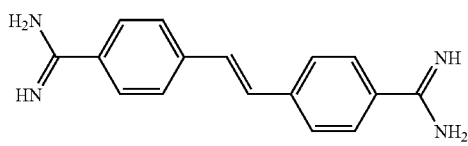
(G-1)

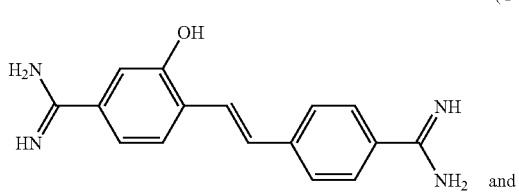
(G-2) and

Each amidine unit may be replaced, independently of one another, by one of the units defined above for $R^8$ and $R^{11}$. As in the case of benzimidazoles and pentamidines, salts of stilbamidine, hydroxystilbamidine and indole derivatives thereof are also suitable for the process according to the invention. Preferred salts include, for example, dihydrochloride and methanesulfonate salts.

Still other analogues are those which fall under a formula which are provided in one of the U.S. Pat. Nos. 5,428,051, 5,521,189, 5,602,172, 5,643,935, 5,723,495, 5,843,980, 6,172,104 and 6,326,395 or the US patent application with the publication no. US 2002/0019437 A1, each of which is incorporated in its entirety by way of reference. Illustrative analogues include 1,5-bis(4'-(N-hydroxyamidino)phenoxy) pentane, 1,3-bis(4'-(N-hydroxyamidino)phenoxy)propane, 1,3-bis(2'-methoxy-4'-(N-hydroxyamidino)phenoxy)propane, 1,4-bis(4'-(N-hydroxyamidino)phenoxy)butane, 1,5-bis(4'-(N-hydroxyamidino)phenoxy)pentane, 1,4-bis(4'-(N-hydroxyamidino)phenoxy)butane, 1,3-bis(4'-(4-hydroxyamidino)phenoxy)propane, 1,3-bis(2'-methoxy-4'-(N-hydroxyamidino)phenoxy)propane, 2,5-bis[4-amidinophenyl]furan, 2,5-bis[4-amidinophenyl]furan bisamide oxime, 2,5-bis[4-amidinophenyl]furan bis-O-methylamide oxime, 2,5-bis[4-amidinophenyl]furan bis-O-ethylamide oxime, 2,8-diamidinodibenzothiophene, 2,8-bis(N-isopropylamidino)carbazole, 2,8-bis-(N-hydroxyamidino)carbazole, 2,8-bis(2-imidazolinyl)dibenzothiophene, 2,8-bis(2-imidazolinyl)-5,5-dioxodibenzothiophene, 3,7-diamidinodibenzothiophene, 3,7-bis(N-isopropylamidino)dibenzothiophene, 3,7-bis(N-hydroxyamidino)dibenzothiophene, 3,7-diaminodibenzothiophene, 3,7-dibromodibenzothiophene, 3,7-dicyanodibenzothiophene, 2,8-diamidinodibenzofuran, 2,8-di-(2-imidazolinyl)dibenzofuran, 2,8-di-(N-isopropylamidino) dibenzofuran, 2,8-di-(N-hydroxylamidino)dibenzofuran, 3,7-di-(2-imidazolinyl)dibenzofuran, 3,7-di(isopropylamidino)dibenzofuran, 3,7-di-(A-hydroxylamidino)dibenzofuran, 2,8-dicyanodibenzofuran, 4,4'-dibromo-2,2'-dinitrobiphenyl, 2-methoxy-2'-nitro-4,4'-dibromobiphenyl, 2-methoxy-2'-amino-4,4'-dibromobiphenyl, 3,7-dibromodibenzofuran, 3,7-dicyanodibenzofuran, 2,5-bis(5-amidino-2-benzimidazolyl)pyrrole, 2,5-bis[5-(2-imidazolinyl)-2-benzimidazolyl]pyrrole, 2,6-bis[5-(2-imidazolinyl)-2-benzimidazolyl]pyridine, 1-methyl-2,5-bis(5-amidino-2-benzimidazolyl)pyrrole, 1-methyl-2,5-bis[5-(2-imidazolyl)-2-benzimidazolyl]pyrrole, 1-methyl-2,5-bis[5-(1,4,5,6-tetrahydro-2-pyrimidinyl)-2-benzimidazolyl]pyrrole, 2,6-bis (5-amidino-2-benzimidazoyl)pyridine, 2,6-bis[5-(1,4,5,6-tetrahydro-2-pyrimidinyl)-2-benzimidazolyl]pyridine, 2,5-bis(5-amidino-2-benzimidazolyl)furan, 2,5-bis[5-(2-imidazolinyl)-2-benzimidazolyl]furan, 2,5-bis(5-N-isopropylamidino-2-benzimidazolyl)furan, 2,5-bis(4-guanylphenyl)furan, 2,5-bis(4-guanylphenyl)-3,4-dimethylfuran, 2,5-di-p-[2-(3,4,5,6-tetrahydropyrimidyl) phenyl]furan, 2,5-bis[4-(2-imidazolinyl)phenyl]furan, 2,5-[bis{4-(2-tetrahydropyrimidinyl)}phenyl]-p-(tolyloxy) furan, 2,5-[bis{4-(2-imidazolinyl)}phenyl]-3-p-(tolyloxy) furan, 2,5-bis{4-[5-(N-2-aminoethylamido)benzimidazol-2- yl]phenyl}furan, 2,5-bis[4-(3a,4,5,6,7,7a-hexahydro-1H-benzimidazol-2-yl)phenyl]furan, 2,5-bis[4-(4,5,6,7-tetrahydro-1H-1,3-diazepin-2-yl)phenyl]furan, 2,5-bis(4-N,N-dimethylcarboxhydrazidophenyl)furan, 2,5-bis{4-[2-(N-2-hydroxyethyl)imidazolinyl]phenyl}furan, 2,5-bis[4-(N-isopropylamidino)phenyl]furan, 2,5-bis{4-[3-(dimethylaminopropyl)amidino]phenyl}furan, 2,5-bis{4-[N-(3-aminopropyl)amidino]phenyl}furan, 2,5-bis[2-(imidzaolinyl)phenyl]-3,4-bis(methoxymethyl)furan, 2,5-bis[4-N-(dimethylaminoethyl)guanyl]phenylfuran, 2,5-bis{4-[(N-2-hydroxyethyl)guanyl]phenyl}furan, 2,5-bis[4-N-(cyclopropylguanyl)phenyl]furan, 2,5-bis[4-(N,N-diethylaminopropyl)guanyl]phenylfuran, 2,5-bis{4-[2-(N-ethylimidazolinyl)]phenyl}furan, 2,5-bis{4-[N-(3-pentylguanyl)]}phenylfuran, 2,5-bis[4-(2-imidazolinyl)phenyl]-3-methoxyfuran, 2,5-bis[4-(N-isopropylamidino)phenyl]-3-methylfuran, bis[5-amidino-2-benzimidazolyl]methane, bis[5-(2-imidazolyl)-2-benzimidazolyl]methane, 1,2-bis[5-amidino-2-benzimidazolyl]ethane, 1,2-bis[5-(2-imidazolyl)-2-benzimidazolyl]ethane, 1,3-bis[5-amidino-2-benzimidazolyl]propane, 1,3-bis[5-(2-imidazolyl)-2-benzimidazolyl]propane, 1,4-bis[5-amidino-2-benzimidazolyl]propane, 1,4-bis[5-(2-imidazolyl)-2-benzimidazolyl]butane, 1,8-bis[5-amidino-2-benzimidazolyl]octane, trans-1,2-bis[5-amidino-2-benzimidazolyl]ethene, 1,4-bis[5-(2-imidazolyl)-2-benzimidazolyl]-1-butene, 1,4-bis[5-(2-imidazolyl)-2-benzimidazolyl]-2-butene, 1,4-bis[5-(2-imidazolyl)-2-benzimidazolyl]-1-methylbutane, 1,4-bis[5-(2-imidazolyl)-2-benzimidazolyl]-2-ethylbutane, 1,4-bis[5-(2-imidazolyl)-2-benzimidazolyl]-1-methyl-1-butene, 1,4-bis[5-(2-imidazolyl)-2-benzimidazolyl]-2,3-diethyl-2-butene, 1,4-bis[5-(2-imidazolyl)-2-benzimidazolyl]-1,3-butadiene, 1,4-bis[5-(2-imidazolyl)-2-benzimidazolyl]-2-methyl-1,3-butadiene, bis[5-(2-pyrimidyl)-2-benzimidazolyl]methane, 1,2-bis[5-(2-pyrimidyl)-2-benzimidazolyl]ethane, 1,3-bis[5-amidino-2-benzimidazolyl]propane, 1,3-bis[5-(2-pyrimidyl)-2-benzimidazolyl]propane, 1,4-bis[5-(2-pyrimidyl)-2-benzimidazolyl]butane, 1,4-bis-[5-(2-pyrimidyl)-2-benzimidazolyl]-1-butene, 1,4-bis[5-(2-pyrimidyl)-2-benzimidazolyl]-2-butene, 1,4-bis[5-(2-pyrimidyl)-2-benzimidazolyl]-1-methylbutane, 1,4-bis[5-(2-pyrimidyl)-2-benzimidazolyl]-2-ethylbutane, 1,4-bis[5-(2-pyrimidyl)-2-benzimidazolyl]-1-methyl-1-butene, 1,4-bis[5-(2-pyrimidyl)-2-benzimidazolyl]-2,3-diethyl-2-butene, 1,4-bis[5-(2-pyrimidyl)-2-benzimidazolyl]-1,3-butadiene and 1,4-bis[5-(2-pyrimidyl)-2-benzimidazolyl]-2-methyl-1,3-butadiene, 2,4-bis(4-guanylphenyl)pyrimidine, 2,4-bis(4-imidazolin-2-yl)pyrimidine, 2,4-bis[(tetrahydropyrimidinyl-2-yl)phenyl]pyrimidine, 2-(4-[N-i-propylguanyl]phenyl)-4-(2-methoxy-4-[N-i-propylguanyl]phenyl)pyrimidine, 4-(N-cyclopentylamidino)-1,2-phenylenediamine, 2,5-bis[2-(5-amidino)benzimidazoyl]furan, 2,5-bis[2-{5-(2-imidazolino)}benzimidazoyl]furan, 2,5-bis[2-(5-N-isopropylamidino)benzimidazoyl]furan, 2,5-bis[2-(5-N-cyclopentylamidino)benzimidazoyl]furan, 2,5-bis[2-(5-amidino)benzimidazoyl]pyrrole, 2,5-bis[2-{5-(2-imidazolino)}benzimidazoyl]pyrrole, 2,5-bis[2-(5-N-isopropylamidino)benzimidazoyl]pyrrole, 2,5-bis[2-(5-N-cyclopentylamidino)benzimidazoyl]pyrrole, 1-methyl-2,5-bis[2-(5-amidino)benzimidazoyl]pyrrole, 2,5-bis[2-{5-(2-imidazolino)}benzimidazoyl]-1-methylpyrrole, 2,5-bis[2-(5-N-cyclopentylamidino)benzimidazoyl]-1-methylpyrrole, 2,5-bis[2-(5-N-isopropylamidino)benzimidazoyl]thiophene, 2,5-bis[2-{5-(2-imidazolino)}benzimidazoyl]pyridine, 2,6-bis[2-(5-amidino)benzimidazoyl]pyridine, 4,4'-bis[2-(5-N-isopropylamidino)benzimidazoyl]-1,2-diphenylethane, 4,4'-bis[2-(5-N-cyclopentylamidino)benzimidazoyl]-2,5-diphenylfuran, 2,5-bis[2-(5-amidino)benzimidazoyl]benzo[b]furan, 2,5-bis[2-(5-N-cyclopentylamidino)benzimidazoyl]-benzo[b]furan, 2,7-bis[2-(5-N-isopropylamidino)benzimidazoyl]fluorine, 2,5-bis[4-(3-(N-morpholinopropyl)carbamoyl)phenyl]furan, 2,5-bis[4-(2-N,N-dimethylaminoethylcarbamoyl)phenyl]furan, 2,5-bis[4-(3-N,N-dimethylaminopropylcarbamoyl)phenyl]furan, 2,5-bis[4-(3-N-methyl-3-N-phenylaminopropylcarbamoyl)phenyl]furan, 2,5-bis[4-(3-N,N8,N11-trimethylaminopropylcarbamoyl)phenyl]furan, 2,5-bis[3-amidinophenyl]furan, 2,5-bis[3-(N-isopropylamidino)amidinophenyl]furan, 2,5-bis[3-[(N-(2-dimethylaminoethyl)amidino]phenylfuran, 2,5-bis[4-(N-2,2,2-trichloroethoxycarbonyl)amidinophenyl]furan, 2,5-bis[4-(N-thioethylcarbonyl)amidinophenyl]furan, 2,5-bis[4-(N-benzyloxycarbonyl)amidinophenyl]furan, 2,5-bis[4-(N-phenoxycarbonyl)amidinophenyl]furan, 2,5-bis[4-(N-(4-fluoro)phenoxycarbonyl)amidinophenyl]furan, 2,5-bis[4-(N-(4-methoxy)phenoxycarbonyl)amidinophenyl]-furan, 2,5-bis[4-(1-acetoxyethoxycarbonyl)amidinophenyl]furan and 2,5-bis[4-(N-(3-fluoro)phenoxycarbonyl)amidinophenyl]furan. Processes for the preparation of one of the above compounds are described in U.S. Pat. Nos. 5,428,051, 5,521,189, 5,602,172, 5,643,935, 5,723,495, 5,843,980, 6,172,104 and 6,326,395 or the US patent application with the publication no. US 2002/0019437 A1.

Pentamidine metabolites are likewise suitable in the antiproliferative combination according to the invention. Pentamidine is rapidly metabolised in the body to at least seven primary metabolites. Some of these metabolites have one or more actions in common with pentamidine Pentamidine metabolites have an antiproliferative action when combined with a benzimidazole or an analogue thereof.

Seven pentamidine analogues are shown below.

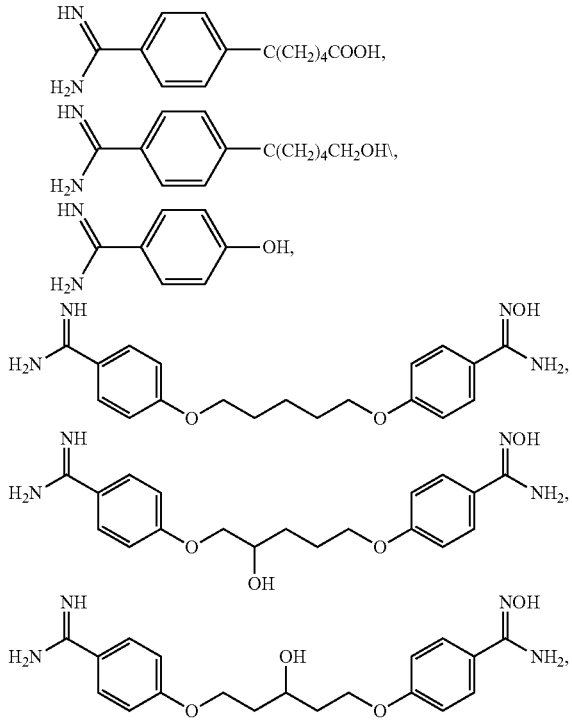

-continued

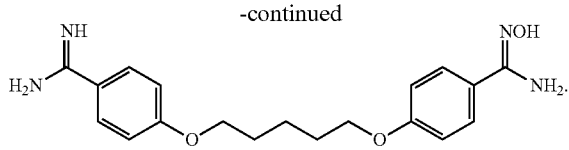

The combinations according to the invention of compounds of the formula I and formula V or analogues thereof and metabolites thereof are suitable for the treatment of neoplasms. Combination therapy can be carried out alone or in combination with another therapy (for example operation, irradiation, chemotherapy, biological therapy). In addition, a person whose risk of developing a neoplasm is greater (for example someone who is genetically predisposed or someone who previously had a neoplasm) can be given prophylactic treatment in order to inhibit or delay neoplasm formation.

The invention likewise relates to the combination of kinesin ATPase Eg5/KSP with the compounds of the formula V, pentamidine, analogues thereof and/or metabolites thereof.

The dosage and frequency of administration of each compound in the combination can be controlled independently. For example, one compound may be administered orally three times daily, while the second compound may be administered intramuscularly once per day. The compounds may also be formulated together, leading to administration of both compounds.

The antiproliferative combinations according to the invention can also be provided as components of a pharmaceutical package. The two medicaments can be formulated together or separately and in individual dosage amounts.

Under another aspect, the invention encompasses a [lacuna] for the treatment of a patient who has a neoplasm, such as a cancer, by administration of a compound of the formula (I) and (V) in combination with an antiproliferative agent. Suitable antiproliferative agents include those provided in Table 1.

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$

FAB (fast atom bombardment) $(M+H)^+$

ESI (electrospray ionisation) $(M+H)^+$

APCI-MS (atmospheric pressure chemical ionisation-mass spectrometry) $(M+H)^+$

EXAMPLE 1

Synthesis of N-(2-dimethylaminoethyl)-N'-((2R,4aS, 5R,10bS)-5-phenyl-9-trifluoromethyl-3,4,4a,5,6,10b-hexahydro-2H-pyrano[3,2-c]quinolin-2-ylmethyl) oxalamide 3

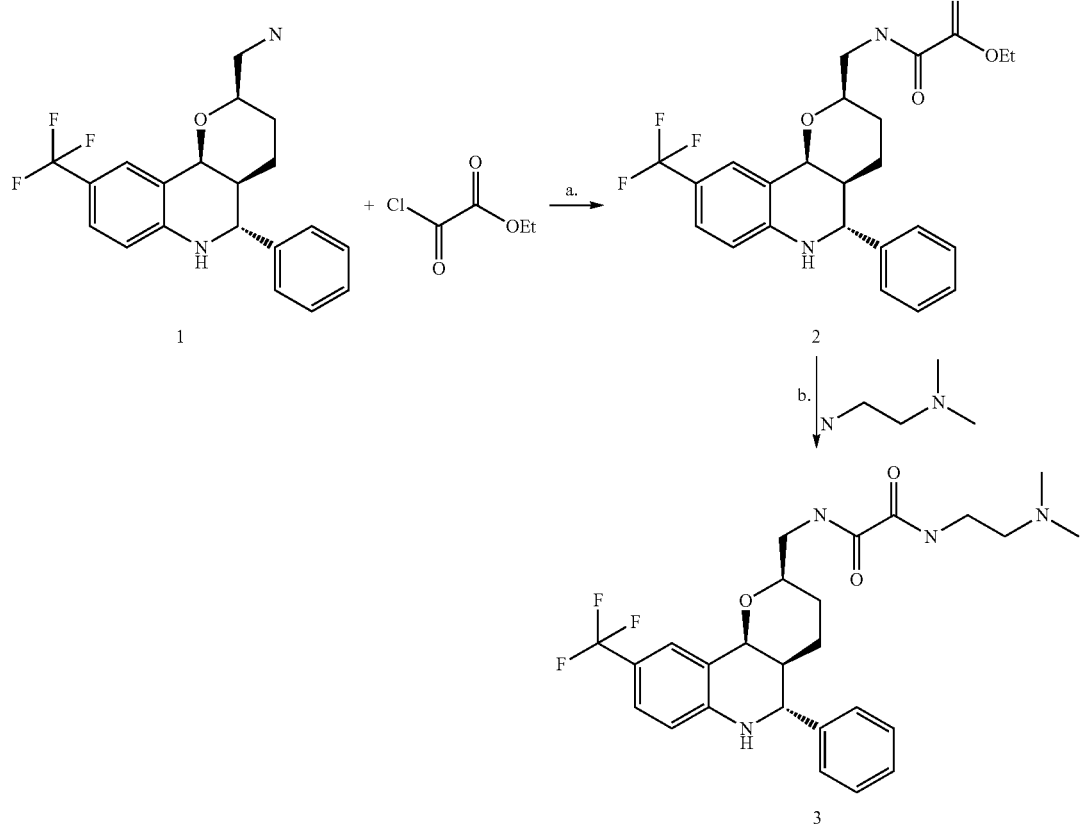

a. Compound 1 (300 mg, 0.83 mmol) was dissolved in DCM (3 ml), pyridine (0.1 ml) was added at RT, and ethyl chloroformylformate (0.1 ml, 0.91 mmol) was added dropwise at RT. The mixture was stirred at RT for a further 18 h, diluted with 20 ml of DCM and washed by shaking 2× with 1 N HCl solution, and the organic phase was rinsed with water, dried and evaporated to dryness in vacuo. The colourless product obtained in clean form was reacted without further purification (colourless solid 2, 345 mg, 90%).

b. Compound 2 (206 mg, 0.45 mmol) was dissolved in EtOH (3 ml), N,N-dimethylethylenediamine (53 l, 0.49 mmol) was added, and the mixture was stirred at RT for a further 18 h. The reaction solution was evaporated to dryness and separated by column chromatography (ethyl acetate/cyclohexane), giving a colourless solid (205 mg, 0.41 mmol, 91%), which proved to be compound 3.

EXAMPLE 2

Synthesis of 3-amino-4-[((2R,4aS,5R,10bS)-5-phenyl-9-trifluoromethyl-3,4,4a,5,6,10b-hexahydro-2H-pyrano[3,2-c]quinolin-2-ylmethyl)amino]-cyclobut-3-ene-1,2-dione 4 and similar compounds

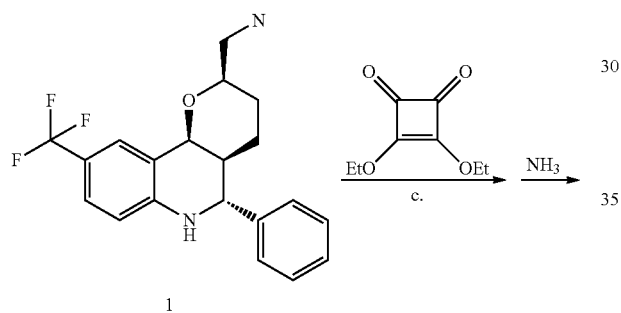

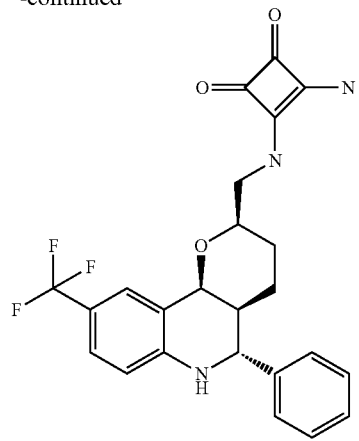

C. Analogous 2-step reactions were carried out with the starting material 1 and the following substrates (for example see above):

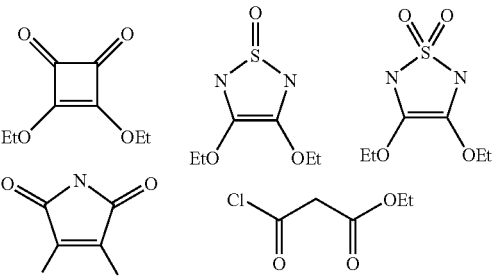

EXAMPLE 3

Synthesis of 2-[((2R,4aS,5R,10bS)-5-phenyl-9-trifluoromethyl-3,4,4a,5,6,10b-hexahydro-2H-pyrano[3,2-c]quinolin-2-ylmethyl)amino]thiazole-4-carboxylic acid (2-dimethylaminoethyl)amide 7

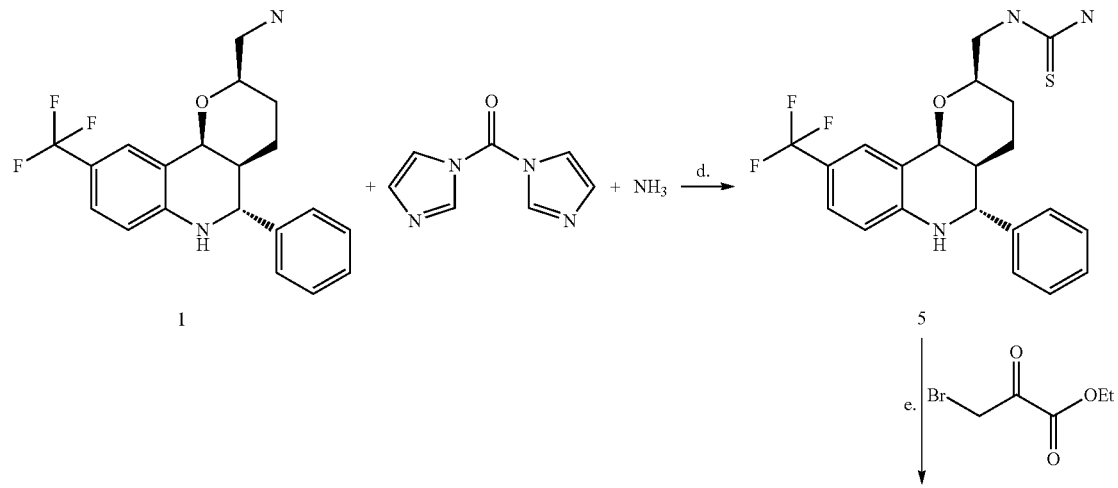

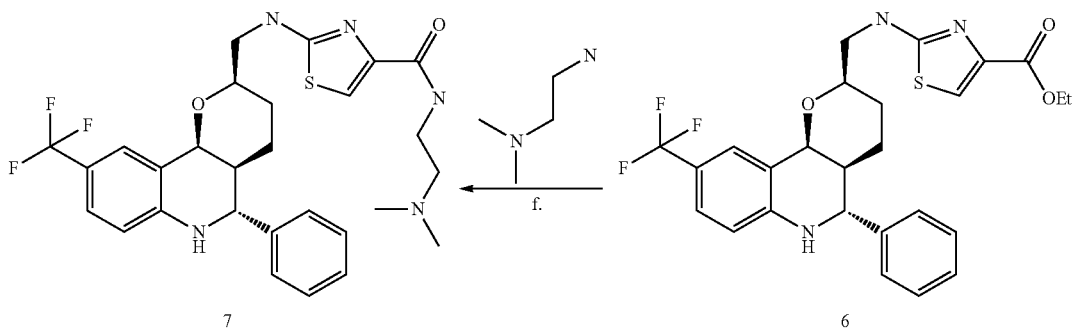

d. Compound 1 (200 mg, 0.55 mmol) was dissolved in 5 ml of THF/DMF (1:1), thiocarbonylimidazole (98.3 mg, 0.55 mmol) was added, and the mixture was stirred at RT for 15 h. Ammonia solution (0.68 ml, 25% in water) was subsequently added, and the mixture was stirred at RT for a further 2.5 h. The reaction solution was freed from the readily volatile solvents, and water was added to the residue. The precipitated solid was filtered off, rinsed with water and purified by column chromatography (ethyl acetate/cyclohexane), giving a colourless solid (5, 175 mg, 0.42 mmol, 75%).

e. Compound 5 (94 mg, 0.22 mmol) was dissolved in 2 ml of THF/DMF (1:1), ethyl bromopyruvate (43.5 mg, 0.22 mmol) was added, and the mixture was stirred at 70° C. for 15 h. The reaction solution was freed from the readily volatile solvents, and water was added to the residue. The precipitated solid was filtered off and dried in vacuo, giving a colourless solid (6, 88 mg, 0.17 mmol, 76%).

f. Compound 6 (55 mg, 0.11 mmol) was dissolved in 2 ml of ethanol, N,N-dimethylethylenediamine (13 l, 0.12 mmol) was added, and the mixture was stirred under reflux for 15 h. Water was added to the reaction solution. The precipitated solid was filtered off, rinsed with water and purified by column chromatography (ethyl acetate/cyclohexane), giving a colourless solid (7, 32 mg, 0.06 mmol, 53%).

EXAMPLE 4

Synthesis of N-((4aS,5R,10bS)-5-phenyl-9-trifluoromethyl-3,4,4a,5,6,10b-hexahydro-2H-pyrano[3,2-c]quinolin-2-ylmethyl)-4H-1,2,4-triazole-3,5-diamine 9 and N-cyano-N'-((4aS,5R,10bS)-5-phenyl-9-trifluoromethyl-3,4,4a,5,6,10b-hexahydro-2H-pyrano[3,2-c]quinolin-2-ylmethyl)-(2-dimethylaminoethyl)guanidine 10

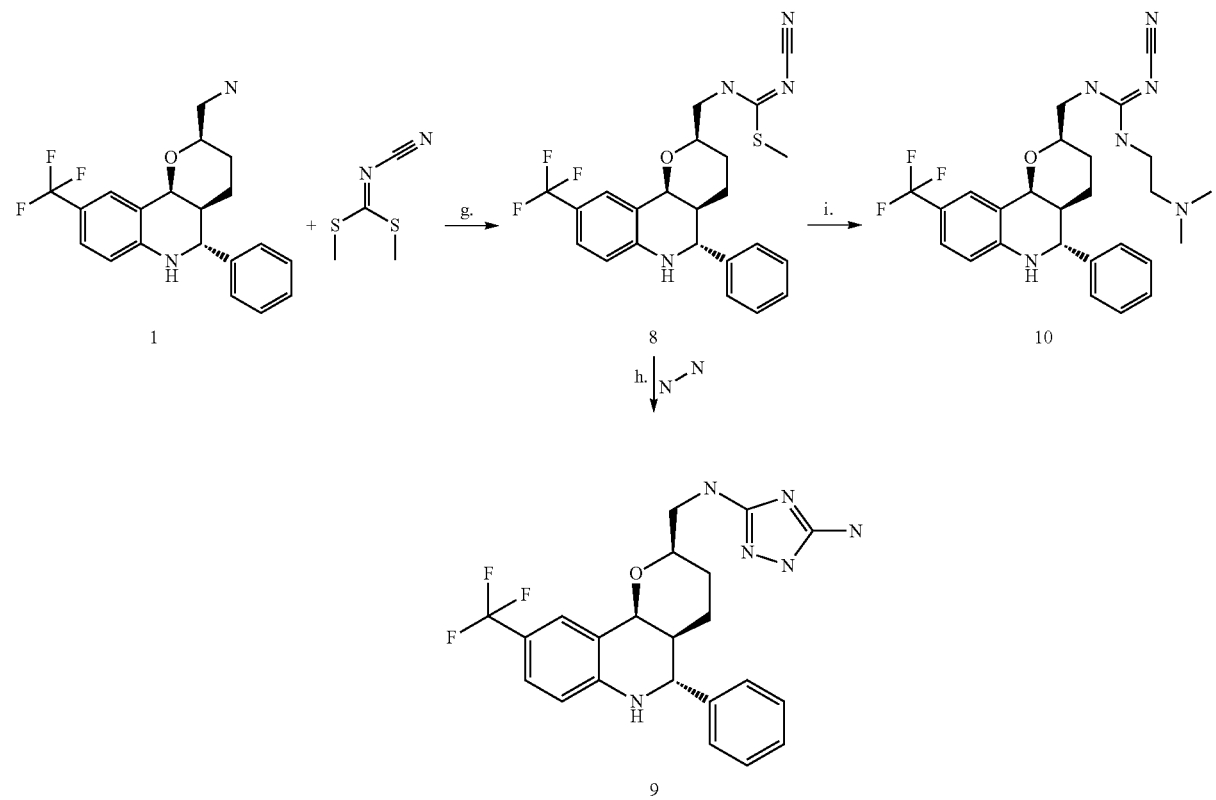

g. Compound 1 (300 mg, 0.83 mmol) was dissolved in 8 ml of ethanol, dimethyl cyanodithioiminocarbonate (120 mg, 0.83 mmol) was added, and the mixture was stirred at 50° C. for 15 h. The reaction solution was evaporated to dryness in vacuo, and the brownish residue was reacted further without further purification.

h. Half of the crude compound 8 (about 190 mg, 0.41 mmol) was taken up in 5 ml of ethanol, hydrazinium hydroxide (1 ml) was added, and the mixture was stirred at 80° C. for 2 h in a pressure flask. The reaction suspension was evaporated to dryness in vacuo, the brownish residue was suspended in MeOH (10 ml)), and water (10 ml) was added. The beige residue which formed was filtered off, rinsed with water and dried, giving a beige solid (9, 149 mg, 0.34 mmol, 82%).

i. The other half of the crude compound 8 (about 190 mg, 0.41 mmol) was taken up in 10 ml of THF, N,N-dimethylethylenediamine (72 mg, 0.83 mmol) was added, and the mixture was stirred at 80° C. for 2 h. The reaction suspension was evaporated to dryness in vacuo, the brownish residue was suspended in MeOH (10 ml)), and water (10 ml) was added. The residue which formed was filtered off, rinsed with water and dried, giving a colourless solid (10, 141 mg, 0.28 mmol, 69%).

The following compounds according to the invention are obtained analogously using or corresponding precursors:

| Example | | | [M + 1]$^+$ | Rt (HPLC) [min] |
|---|---|---|---|---|
| (5) | ABS | | 487 | 5.63 |
| (6) | ABS | | 530 | 4.13 |
| (7) | ABS | | 513 | 4.35 |

| Example | | [M + 1]⁺ | Rt (HPLC) [min] |
|---|---|---|---|
| (8) | ABS | 506 | 4.4 |
| (9) | ABS | 478 | 4.96 |
| (10) | ABS | 532 | 4.48 |
| (11) | ABS | 578 | 5.81 |

-continued
| Example | | [M + 1]+ | Rt (HPLC) [min] |
|---|---|---|---|
| (12) | ABS 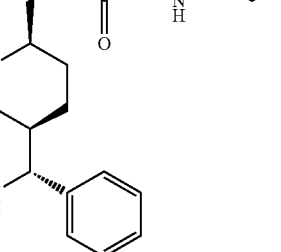 | 520 | 4.37 |
| (13) | ABS 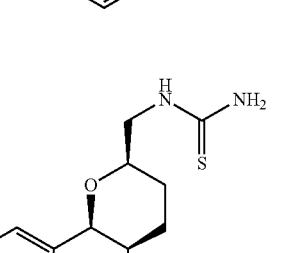 | 422 | 5.31 |
| (14) | ABS 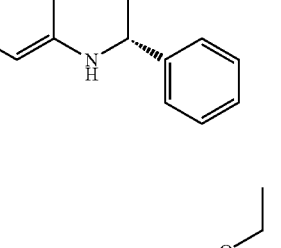 | 508 | 5.76 |
| (15) | ABS 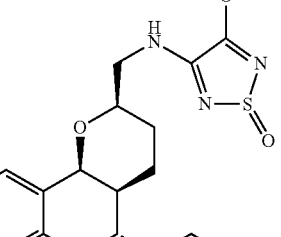 | 479 | 4.83 |

-continued

| Example | | [M + 1]⁺ | Rt (HPLC) [min] |
|---|---|---|---|
| (16) | ABS | 550 | 4.29 |
| (17) | ABS | 519 | 5.65 |
| (18) | ABS | 546 | 4.59 |

| Example | | [M + 1]+ | Rt (HPLC) [min] |
|---|---|---|---|
| (19) | ABS 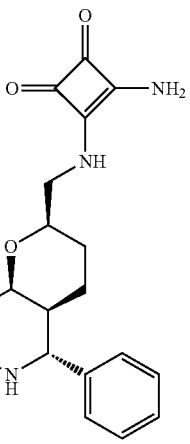 | 458 | 4.75 |
| (20) | ABS 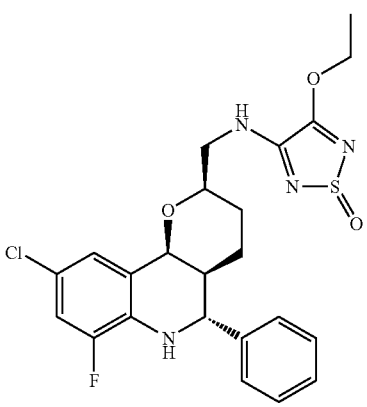 | 492 | 5.84 |
| (21) | ABS 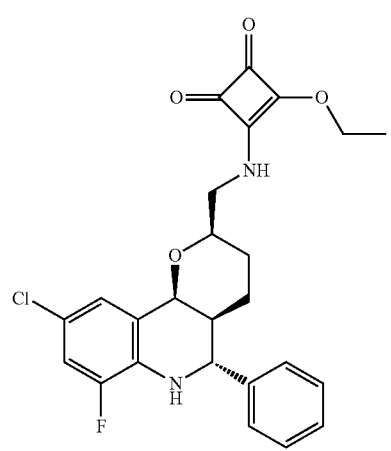 | 472 | 5.84 |

-continued

| Example | | [M + 1]⁺ | Rt (HPLC) [min] |
|---|---|---|---|
| (22) | ABS | 534 | 4.24 |
| (23) | ABS | 514 | 4.05 |
| (24) | ABS | 561 | 4.64 |

| Example | | [M + 1]+ | Rt (HPLC) [min] |
|---|---|---|---|
| (25) | ABS 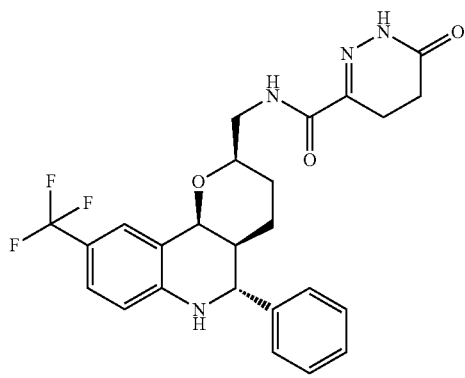 | 487 | 5.2 |
| (26) | ABS 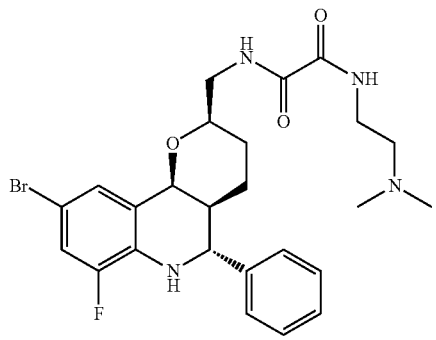 | 534 | 4.48 |
| (27) | ABS 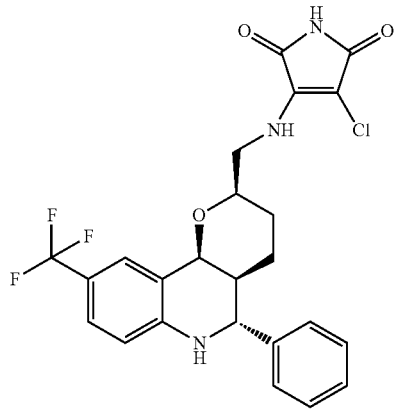 | 493 | 5.92 |

| Example | | [M + 1]+ | Rt (HPLC) [min] |
|---|---|---|---|
| (28) | ABS | 545 | |
| (29) | ABS | 524 | |
| (30) | ABS | 566 | |

| Example | | [M + 1]⁺ | Rt (HPLC) [min] |
|---|---|---|---|
| (31) | RAC | 445 | 4.40 |
| (32) | RAC | 502 | 4.32 |
| (33) | RAC | 520 | 4.16 |

The following examples relate to medicaments:

EXAMPLE C

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE D

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE E

Solution

A solution is prepared from 1 g of an active ingredient of the formula 1, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE F

Ointment 500 mg of an active ingredient of the formula I are mixed with 99.5 g of Vaseline under aseptic conditions.

EXAMPLE G

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE H

Dragees

Tablets are pressed analogously to Example E and subsequently coated in a conventional manner with a coating of sucrose, potato starch, talc, tragacanth and dye.

EXAMPLE I

Capsules 2 kg of active ingredient of the formula I are introduced into hard gelatine capsules in a conventional manner in such a way that each capsule contains 20 mg of the active ingredient.

EXAMPLE J

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. Compounds of the formula I

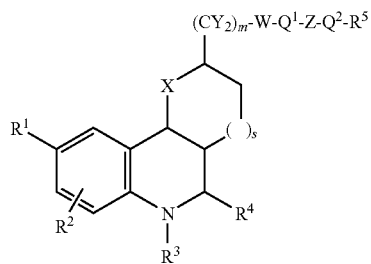

in which
$R^1$ denotes H, A, Hal, SA, $(CH_2)_pCN$, SCN, $(CF_2)_pCF_3$, $SF_5$, OA, $O(CF_2)_pCF_3$, $S(CF_2)_pCF_3$, $NR_2$, NRCOR, $NRSO_2R$, $NR(CH_2)_pNR_2$, $CONR(CH_2)_pNR_2$, $SO_2NR(CH_2)_pNR_2$, $CONR_2$, $SO_2NR_2$, or COOR,
$R^2$ denotes H or Hal
$R^3$ denotes H or A
A denotes linear or branched alkyl having 1 to 10 C atoms or cycloalkyl having 3 to 7 C atoms,
$R^4$ denotes aryl or heteroaryl, each of which is optionally substituted by Hal, $NO_2$, CN, OR, A, $—(CY_2)_n—OR$, $—OCOR$, $—(CY_2)_n—CO_2R$, $—(CY_2)_n—CN$ or $—(CY_2)_n—NR_2$, or
$R^4$ denotes aryl or heteroaryl each of which is unsubstituted or mono- or polysubstituted by aryl or heteroaryl, where each of the optional aryl or heteroaryl substituents are optionally substituted by Hal, $NO_2$, CN, A, OR, OCOR, $NR_2$, $CF_3$, $OCF_3$, $OCH(CF_3)_2$,
X denotes O,
Y denotes H, A, Hal or OR
R denotes H, A, $(CH_2)_pO(CH_2)_pR^3$ or $(CH_2)_pNA(CH_2)_pR^3$,
W denotes $CH_2$, C=O or C=S,
$Q^1$ denotes NR, O or S,
Z denotes —SO—,

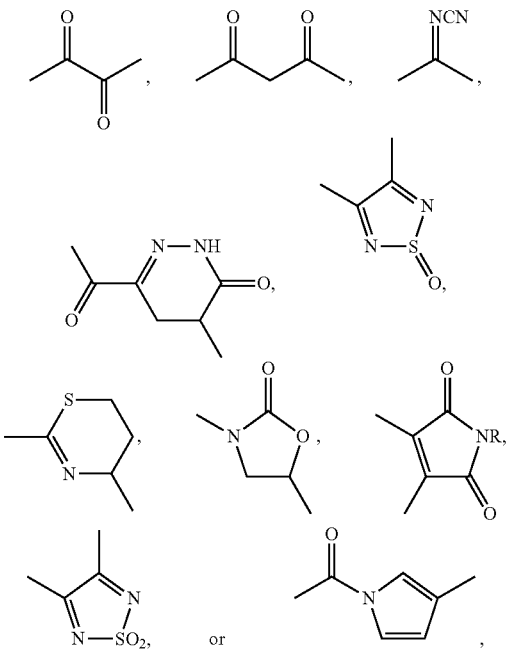

$Q^2$ denotes NR, S, O or a single bond,
$R^5$ denotes H, $(CY_2)_pNR_2$, $(CY_2)_pOR$, $(CY_2)_pSR$,

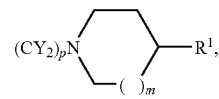

$(CY_2)_pQ^1COQ^1R$ or $(CY_2)_pCOOR$ and, if $Q^2$ denotes a single bond, also Hal,
Hal denotes F, Br or Cl
n denotes 1, 2, 3 or 4,
m denotes 0, 1 or 2,
p denotes 0, 1, 2, 3, 4, 5, 6, 7 or 8
and
s denotes 0, 1 or 2,
and pharmaceutically usable tautomers, salts and stereoisomers thereof, including mixtures thereof in all ratios.
2. Compounds according to claim 1, in which $R^1$, denotes alkyl, $CF_3$, $OCF_3$, SCN, $CH_2CN$, OA, SA, Hal or $SCF_3$.
3. Compounds according to claim 1, in which $R^2$, denotes H or F.
4. Compounds according to claim 1, in which $R^3$, denotes H, methyl, ethyl, n-propyl or n-butyl.
5. Compounds according to claim 1, in which $R^4$, denotes aryl, which may be substituted by F, Cl, OR or aryl.
6. Compounds according to claim 1, in which W, denotes $CH_2$ or C=O.

7. Compounds according to claim 1, in which Z denotes

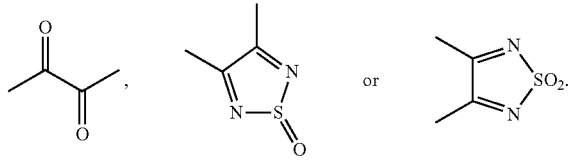

8. Compounds according to claim 1, in which $Q^1$ and $Q^2$, independently of one another, denote NR or O.

9. Compounds according to claim 1, in which $R^5$ denotes H, $(CY_2)_pNR_2$, $(CY_2)_pOR$,

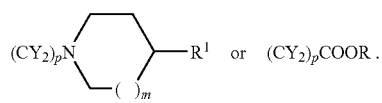

10. Compounds according to claim 1, in which R denotes H, A or $(CH_2)_pNA(CH_2)_pR^3$.

11. Compounds according to claim 1, of the sub-formulae IA or IB:

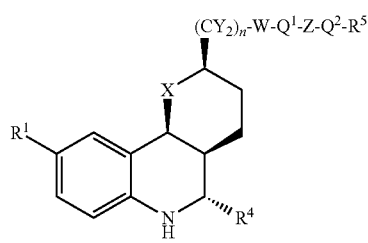

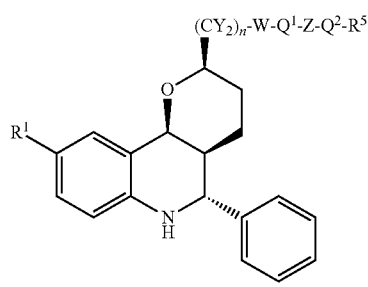

in which $R^1$, $R^4$, $R^5$, X, W, Z, $Q^1$, $Q^2$ and Y have the meanings indicated above.

12. Process for the preparation of compounds of the formula I of claim 1 and pharmaceutically usable salts, tautomers and stereoisomers thereof, comprising:

reacting compounds of the formula II

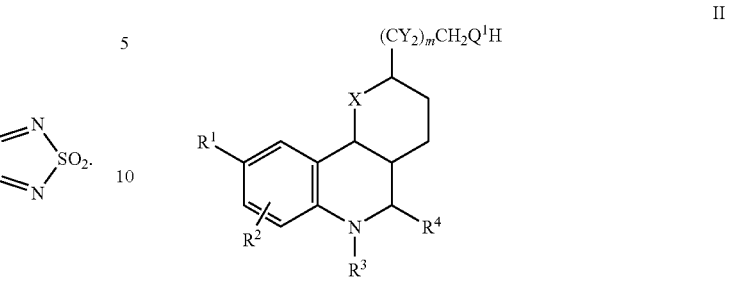

in which $R^1$, $R^2$, $R^3$, $R^4$, X, Y, $Q^1$ and m have the meanings indicated above, and W denotes $CH_2$ with compounds of the formula III $$L\text{-}Z\text{-}Q^2\text{-}R^5 \qquad \text{III}$$

in which Z, $Q^2$, $R^5$ have the meanings indicated above and L denotes a leaving group, and/or a base or acid of the formula I is optionally converted into one of its salts.

13. A medicament composition comprising at least one compound of the formula I according to claim 1 and/or pharmaceutically usable salts, tautomers and stereoisomers thereof, including mixtures thereof in all ratios, and optionally excipients and/or adjuvants.

14. A mixture comprising one or more compounds of the formula I of claim 1 and an amount of one or more compounds of the formula V,

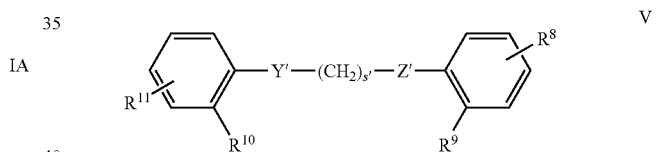

in which
Y' and Z' each, independently of one another, denote O or N, $R^9$ and $R^{10}$ each, independently of one another, denote H, OH, halogen, OC1-10-alkyl, $OCF_3$, $NO_2$ or $NH_2$, s' denotes an integer between 2 and 6, each inclusive, and $R^8$ and $R^{11}$ are each, independently of one another, in the meta- or para-position and are selected from the group:

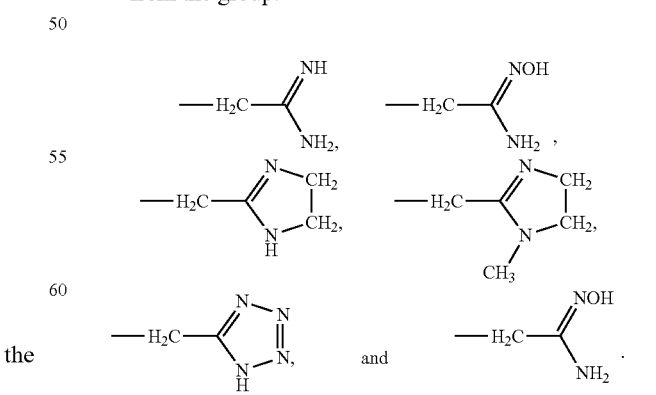

15. Mixture according to claim 14, where the compound of the formula V used is pentamidine or a salt thereof.

16. A compound selected from the following compounds:
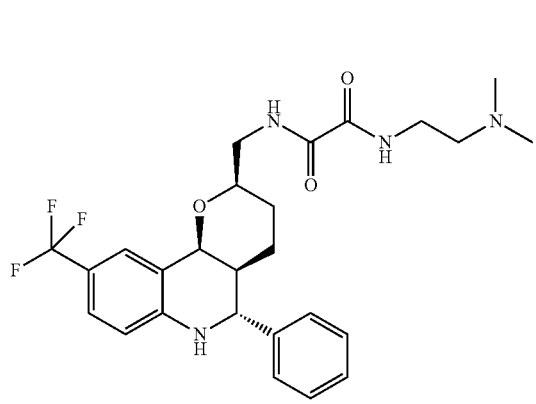
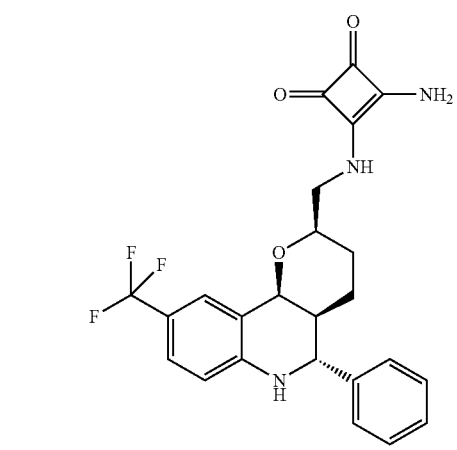
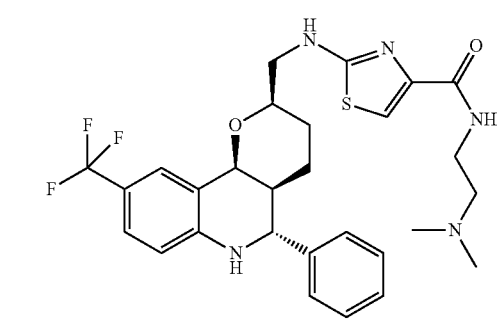
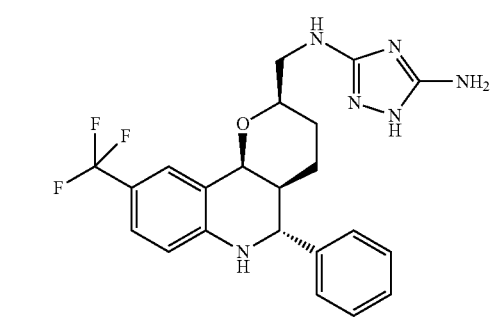
-continued
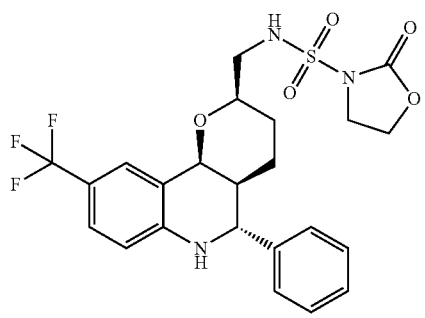
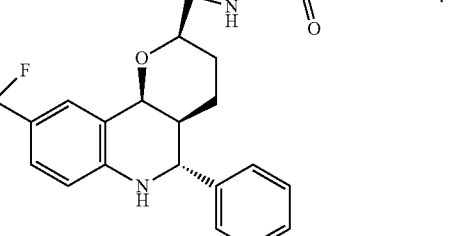
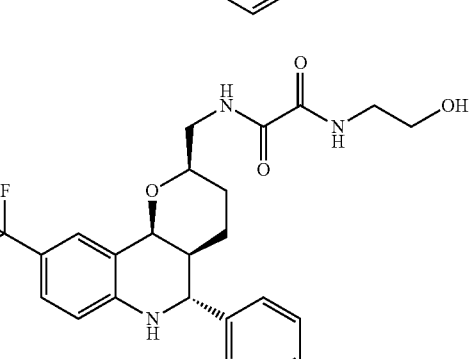
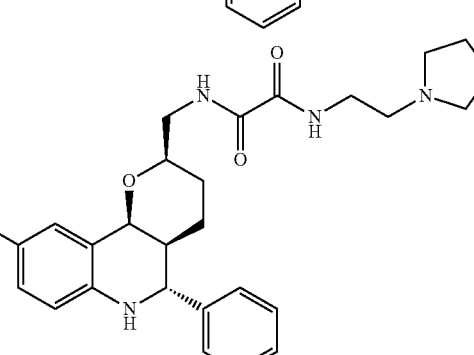
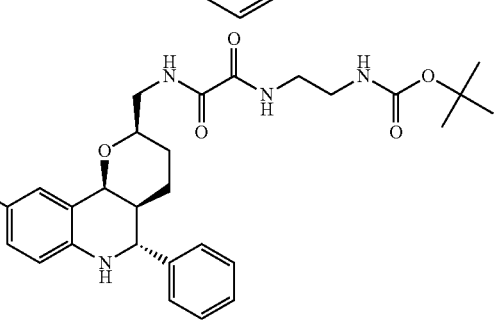

57
-continued
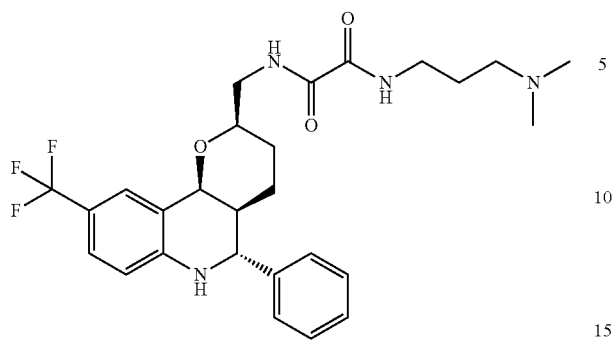
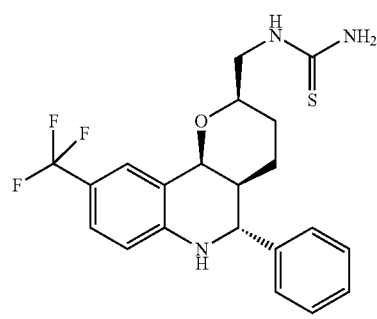
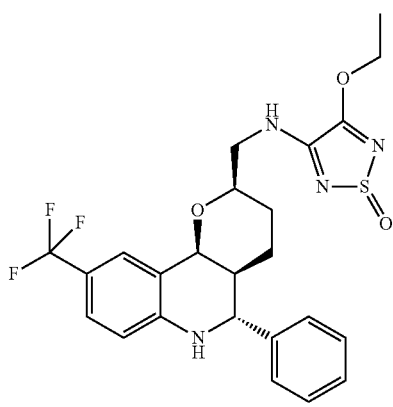
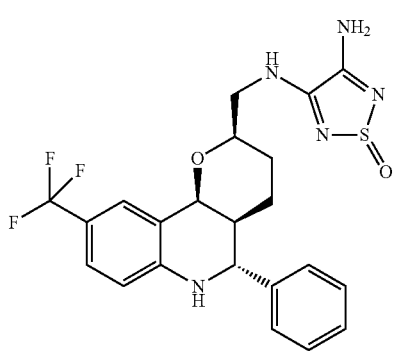
58
-continued
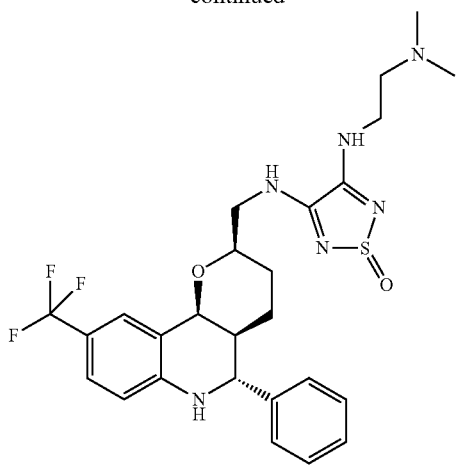
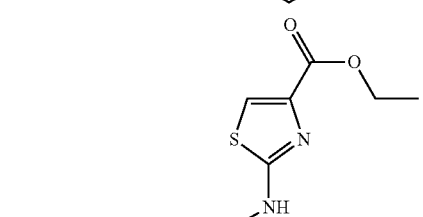
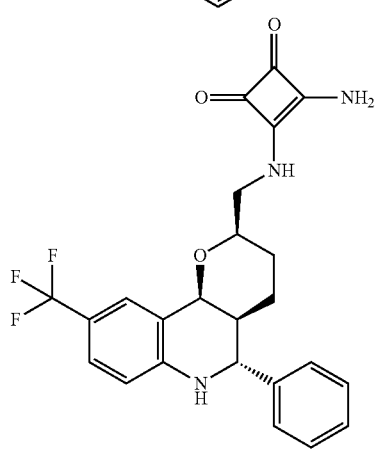

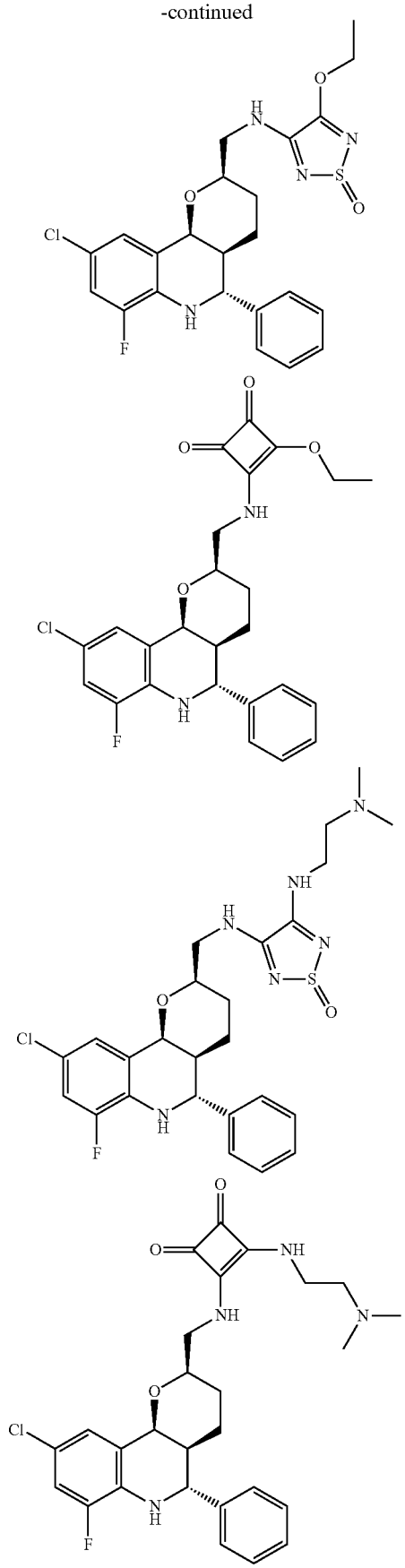
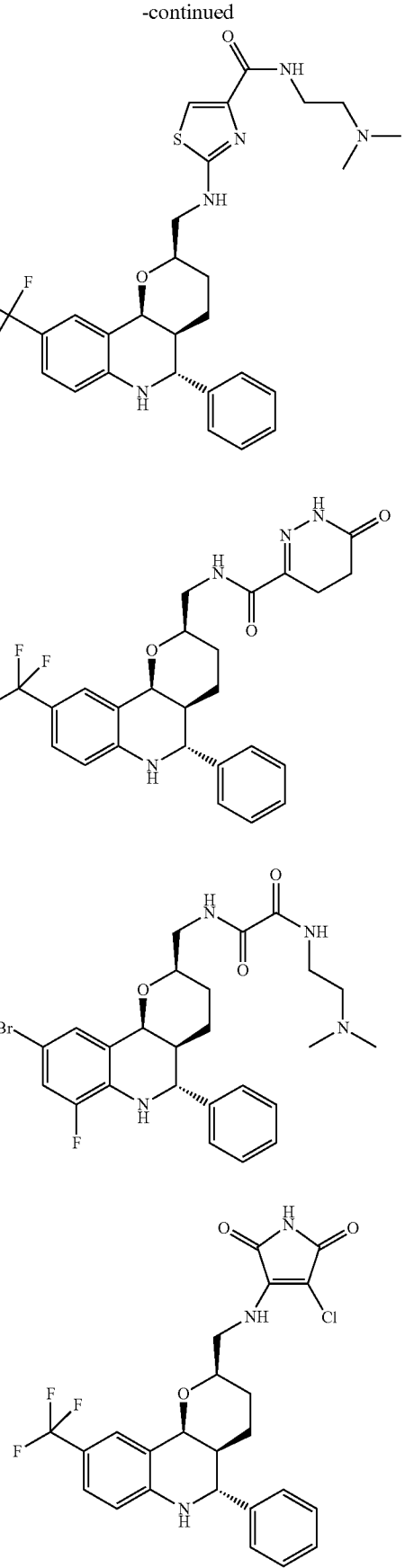

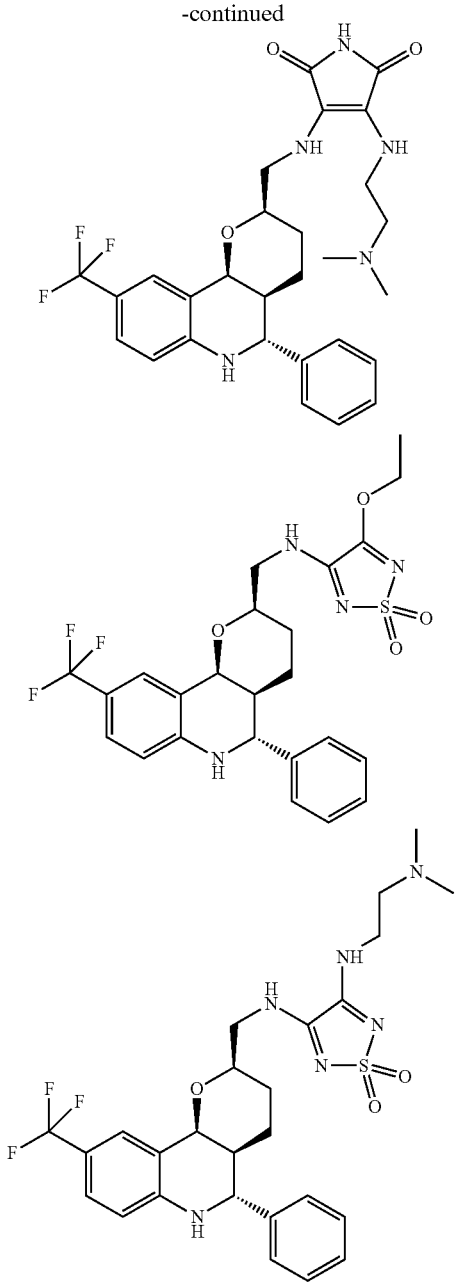
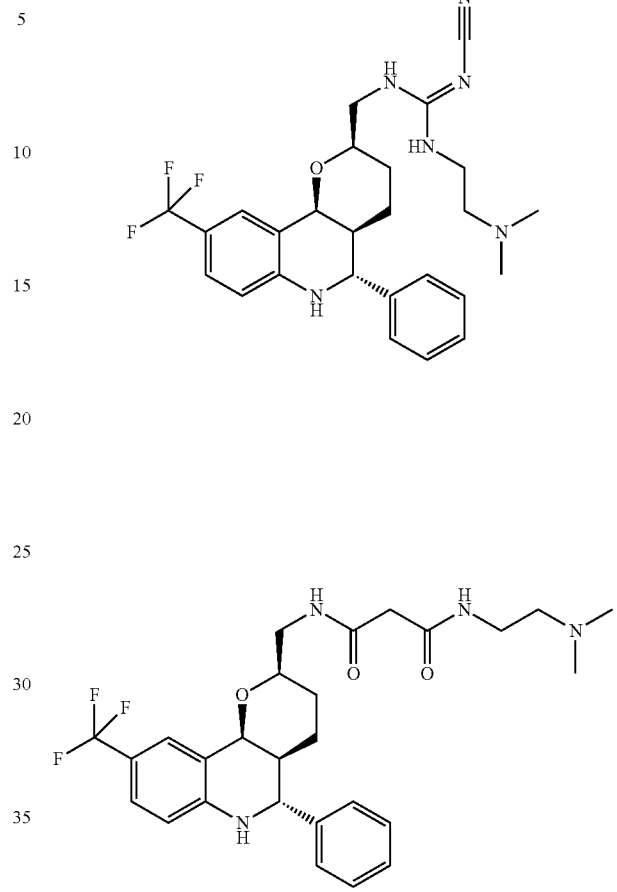
and pharmaceutically usable tautomers, salts and stereoisomers thereof, including mixtures thereof in all ratios.
* * * * *

UNITED STATES PATENT AND TRADEMARK OFFICE
CERTIFICATE OF CORRECTION

PATENT NO. : 8,524,732 B2 Page 1 of 1
APPLICATION NO. : 12/532002
DATED : September 3, 2013
INVENTOR(S) : Schiemann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 768 days.

Signed and Sealed this
Fifteenth Day of September, 2015

Michelle K. Lee
*Director of the United States Patent and Trademark Office*